United States Patent [19]

Tonomura et al.

[11] Patent Number: 5,554,315

[45] Date of Patent: Sep. 10, 1996

[54] FOAMING SURFACTANT COMPOSITION COMPRISING FATTY ACID POLYOXYALKYLENE LOWER ALKYL ETHER AND FATTY ACID MONOGLYCERIDE

[75] Inventors: Manabu Tonomura, Tochigi; Masaaki Iwahashi; Toyomi Koike, both of Wakayama, all of Japan

[73] Assignee: Kao Corporation, Tokyo, Japan

[21] Appl. No.: 364,687

[22] Filed: Dec. 28, 1994

[30] Foreign Application Priority Data

Dec. 28, 1993 [JP] Japan ..................... 5-354071

[51] Int. Cl.$^6$ .................... C11D 1/825; C11D 10/04; C11D 11/00
[52] U.S. Cl. ................. 510/535; 252/356; 510/137; 510/505; 510/506; 510/155; 510/422
[58] Field of Search ................ 252/174.21, 174.22, 252/DIG. 1, 356, 108, 132, 122

[56] References Cited

U.S. PATENT DOCUMENTS

| | | | |
|---|---|---|---|
| 2,577,503 | 12/1951 | Baird et al. | 252/548 |
| 3,726,807 | 4/1973 | Johnson et al. | 252/356 |
| 4,022,808 | 5/1977 | Yoshihara et al. | 554/149 |
| 4,115,415 | 9/1978 | Yoshihara et al. | 554/149 |
| 4,260,813 | 4/1981 | Kametaka et al. | 560/234 |
| 4,840,942 | 6/1989 | Iwasaki et al. | 514/120 |
| 5,220,046 | 6/1993 | Leach et al. | 554/149 |
| 5,368,045 | 11/1994 | Weerasooriya et al. | 554/149 |
| 5,374,750 | 12/1994 | Nakamura et al. | 554/149 |

FOREIGN PATENT DOCUMENTS

| | | |
|---|---|---|
| 0123423 | 10/1984 | European Pat. Off. . |
| 0131393 | 1/1985 | European Pat. Off. . |
| 0617955 | 10/1994 | European Pat. Off. . |
| 2697265 | 4/1994 | France . |
| 1934540 | 2/1971 | Germany . |
| 4227046 | 2/1993 | Germany . |
| 58-217598 | 12/1983 | Japan . |
| 5222396 | 8/1993 | Japan . |
| 5202382 | 8/1993 | Japan . |
| 5202381 | 8/1993 | Japan . |
| 5302096 | 11/1993 | Japan . |

*Primary Examiner*—Paul Lieberman
*Assistant Examiner*—A. Hertzog
*Attorney, Agent, or Firm*—Oblon, Spivak, McClelland, Maier & Neustadt, P.C.

[57] ABSTRACT

A surfactant composition containing a fatty acid polyoxyalkylene lower alkyl ether represented by formula (1):

$$R(OR^1)_nOR^2 \qquad (1)$$

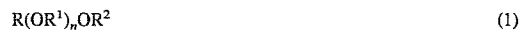

wherein R represents an alkanoyl or alkenoyl group having from 10 to 18 carbon atoms;

$R^1$ represents an alkylene having from 2 to 4 carbon atoms;

$R^2$ represents a lower alkyl group; and n is from 5 to 100 on the average; and a fatty acid monoglyceride represented by formula (2):

$$R^3OCH_2CH(OH)CH_2OH \qquad (2)$$

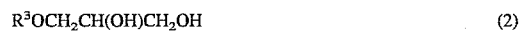

wherein $R^3$ represents an alkanoyl group having from 8 to 16 carbon atoms or an alkenoyl group having from 12 to 22 carbon atoms;

are disclosed.

The foaming properties of a fatty acid polyoxyalkylene lower alkyl ether of formula (1) are improved by adding a fatty acid monoglyceride represented by formula (2) to the fatty acid polyoxyalkylene lower alkyl ether of formula (1).

11 Claims, No Drawings

FOAMING SURFACTANT COMPOSITION COMPRISING FATTY ACID POLYOXYALKYLENE LOWER ALKYL ETHER AND FATTY ACID MONOGLYCERIDE

BACKGROUND OF THE INVENTION

1. Field Of The Invention

This invention relates to a surfactant composition having satisfactory foaming properties, though it comprises a specific nonionic surfactant which has poor foaming properties.

2. Description Of The Background

Nonionic surfactants such as polyoxyethylene surfactants, polyhydric alcohol ester surfactants and ethylene oxide/propylene oxide block copolymer surfactants are generally less irritative to the skin including mucosae. Further, the nonionic surfactants do not ionize over a wide range of pH values ranging from weakly acidic to weakly alkaline, which makes it easy to control the pH of a composition containing these nonionic surfactants. Because of these characteristics, the nonionic surfactants have been employed as emulsifiers or oily stain removers in various products including skin care products, hair care products, kitchen detergents, oral care products, bathing preparations, drugs and cosmetics.

Among the nonionic surfactants, polyoxyethylene nonionic surfactants have been widely employed in particular, since the hydrophilic-hydrophobic balance thereof can be easily controlled by regulating the polyoxyethylene chain length and because they can easily be synthesized.

In general, ester type nonionic surfactants are superior to the corresponding ether surfactants from the viewpoint of biodegradability. Also, the former is less irritative than the latter. Accordingly, ester type surfactants such as those represented by formula (3):

which have an alkanoyl group ($R^0$) derived from a higher fatty acid such as lauric acid, which is a lipophilic group of the polyoxyethylene nonionic surfactant, have been widely employed as emulsifiers. Recently, it has been proposed, for example, in JP-A-4-279552 (the term "JP-A" as used herein means an "unexamined published Japanese patent application") to improve the detergency of a nonionic surfactant represented by formula (3) by etherifying its terminal OH group with a methyl group as shown in formula (4):

wherein $R_0$ represents an alkanoyl group such as lauroyl.

However a polyoxyethylene nonionic surfactant of the ester type represented by formula (4), the terminal of which has been etherified with a lower alkyl group such as a methyl group, exhibits poor foaming properties similar to other nonionic surfactants. Thus, there arises the problem that a detergent, for example, a hair shampoo or a body shampoo containing such a nonionic surfactant fails to lather well and thus cannot give a satisfactory feel in use.

SUMMARY OF THE INVENTION

Accordingly, one object of the present invention is to provide a surfactant composition having excellent foaming properties and which is not very irritative to the skin and mucosae, though it contains an ester type polyoxyethylene nonionic surfactant etherified with a lower alkyl group as the main component.

Briefly, this object and other objects of the invention as hereinafter will become more readily apparent can be attained with a surfactant composition containing a fatty acid polyoxyalkylene lower alkyl ether represented by formula (1):

wherein R represents an alkanoyl or alkenoyl group having from 10 to 18 carbon atoms; $R^1$ represents alkylene having from 2 to 4 carbon atoms; $R^2$ represents a lower alkyl group; and n is from 5 to 100 on the average;

and a fatty acid monoglyceride represented by formula (2):

wherein $R^3$ represents an alkanoyl group having from 8 to 16 carbon atoms or an alkenoyl group having from 12 to 22 carbon atoms.

Another aspect of the invention is a method for improving the foaming properties of a fatty acid polyoxyalkylene lower alkyl ether by adding a fatty acid monoglyceride represented by formula (2) to a fatty acid polyoxyalkylene lower alkyl ether represented by formula (1).

DETAILED DESCRIPTION OF THE INVENTION

It has now been found that the objective of the invention can be achieved by combining a fatty acid monoglyceride, which is a nonionic surfactant, with an ester type polyoxyethylene nonionic surfactant etherified with a lower alkyl group.

In the surfactant composition according to the present invention, the weight ratio of the fatty acid polyoxyalkylene lower alkyl ether represented by formula (1) to the fatty acid monoglyceride represented by formula (2) preferably ranges from 10:1 to 1:2, more preferably from 5:1 to 1:1, from the viewpoint of foaming properties. The total content of the fatty acid polyoxyalkylene lower alkyl ether of formula (1) with the fatty acid monoglyceride of formula (2) preferably ranges from 0.5 to 20% by weight (in terms of the concentration at use) or from 0.5 to 100% by weight (in terms of the content in the final preparation).

In the fatty acid polyoxyalkylene lower alkyl ether of formula (1) to be used in the present invention, group R is an alkanoyl or alkenoyl group having from 10 to 18, preferably from 10 to 14, carbon atoms such as, for example, decanoyl, lauroyl, myristoyl, palmitoyl or oleoyl. Although both straight-chain and branched chain R groups are usable, straight-chain groups are preferred from the viewpoint of foaming properties. Of all the groups, lauroyl and myristoyl groups are preferred. When the group R has less than 10 carbon atoms, only poor foaming properties and detergency are achieved. When the group R contains more than 18 carbon atoms, on the other hand, the resulting product shows insufficient solubility and reduced foaming properties.

The group $R^1$ is an alkylene group having 2 to 4 carbon atoms such as ethylene, propylene, isopropylene, butylene or isobutylene. Of all the groups, the ethylene group is preferred. Alternatively, two or more groups selected from among the above-mentioned groups may be present in a surfactant molecule. For example, a polyoxyalkylene block copolymer obtained by block copolymerization of ethylene oxide with propylene oxide is usable. In formula (1), n, which is the degree of polymerization of the polyoxyalkylene, ranges from 5 to 100, preferably from 10 to 50, on the average. If n is less than 5 on the average, the resulting product has insufficient solubility in water. If n exceeds 100, on the other hand, the resulting product has poor foaming properties and detergency.

Group $R^2$ is a lower alkyl group such as, for example, methyl, ethyl, or isopropyl. From the viewpoint of synthesis procedures and cost, a methyl group is particularly preferred.

As the fatty acid polyoxyalkylene lower alkyl ether represented by formula (1), those produced by known methods as disclosed, for example, in JP-A-53-24930, JP-A-54-1038125, JP-A-56-36431 and JP-A-4-279552, may be employed. However, preferred for use is a fatty acid polyoxyalkylene lower alkyl ether of formula (1) which is obtained by reacting a lower alcohol such as methanol with an alkylene oxide such as ethylene oxide to give a polyoxyalkylene lower alkyl ether, and then reacting this product with a fatty acid, as shown in the following reaction scheme. This method causes little contamination of the product with impurities or by-products.
Reaction scheme

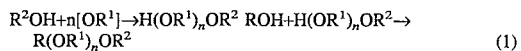

(1)

wherein R, $R^1$ and $R^2$ have each the same meaning as defined above for formula (1); and $[OR^1]$ represents an alkylene oxide having from 2 to 4 carbon atoms.

In the fatty acid monoglyceride of formula (2), group $R^3$ is an alkanoyl group having from 8 to 16, preferably from 10 to 12, carbon atoms such as octanoyl, decanoyl, lauroyl, or palmitoyl or an alkenoyl group having from 12 to 22, preferably from 16 to 20, carbon atoms such as palmitoleyl or oleoyl. When group $R^3$ has carbon atoms in a number outside the range specified above, the fatty acid polyoxyalkylene lower alkyl ether exhibits no improvement in foaming properties.

From the viewpoint of foaming, it is more desirable that the fatty acid monoglyceride of formula (2) contains a lower content of contaminating fatty acid diglycerides and triglycerides. Therefore, it is preferred to refine a marketed product before use by distillation, for example, in order to give a monoglyceride concentration of 80% by weight or above, preferably 90% by weight or above.

In addition to the fatty acid polyoxyalkylene lower alkyl ether of formula (1) and the fatty acid monoglyceride of formula (2), the surfactant composition of the present invention may contain various additives if needed, so long as the low irritativeness quality of the product is not impaired. Examples of such additives include other surfactants such as anionic surfactants, cationic surfactants, other nonionic surfactants and ampholytic surfactants; inorganic salts such as sodium chloride; amino acid salts such as lysine and arginine salts; pH regulators such as citrates; alcohols such as ethanol; propylene glycol, glycerol, sorbitol, polyethylene glycol and alkyl ethers thereof; and water soluble polymers such as xanthan gum, acrylic acid polymers, cationized cellulose, methacrylic acid ampholytic polymers and carboxymethyl cellulose.

Because it is less irritative, the surfactant composition of the present invention is highly applicable to the human body including the face, hands and hair. It can be applied in the form of liquid, cream, gel, mousse, powder or solid. The surfactant composition of the present invention can be packed in containers, for example, bottles, tubes and foamers such as pump foamers and squeeze foamers depending on its form of use.

When the surfactant composition of the present invention is formulated into a liquid preparation, it is usually desirable to use water as the solvent.

The surfactant composition of the present invention can be produced by conventional methods. For example, it can easily be produced by homogenizing the fatty acid polyoxyalkylene lower alkyl ether of formula (1) and the fatty acid monoglyceride of formula (2) optionally together with other additives in a mixer under heat or with the application of a mechanical force.

In the production of products containing the surfactant composition of the present invention, it is convenient to prepare a composition of the fatty acid polyoxyalkylene lower alkyl ether of formula (1) and the fatty acid monoglyceride of formula (2) in advance and then the composition is mixed or dilute with other components according to need. In this instance, it is preferred to blend the components (1) and (2) at a weight ratio of from 10:1 to 1:2, more preferably from 5:1 to 1:1, while heating, if necessary, to give a homogeneous mixture.

The surfactant composition according to the present invention contains the fatty acid polyoxyalkylene lower alkyl ether of formula (1), which is only slightly irritative to the skin and mucosae, together with the fatty acid monoglyceride of formula (2), which is also slightly irritative to the skin and mucosae. Thus, the surfactant composition of the present invention shows sufficient foaming properties while being scarcely irritative to the skin and mucosae.

To further illustrate the present invention in greater detail, the following Examples will be given.

EXAMPLES 1 TO 14 AND COMPARATIVE EXAMPLES 1 TO 6

Each of the compounds (fatty acid polyoxyalkylene lower alkyl ethers) of formula (1) and each of the compounds (fatty acid monoglycerides) of formula (2), as shown in Table 1 infra were homogeneously mixed in a weight ratio of 2:1 to give surfactant compositions. In the Comparative Examples, no compound of formula (2) was employed.

In Table 1, the expression "lauric acid $EO_{15}OMe$", for example, means a compound of formula (1), wherein R is $C_{11}H_{23}CO$, $R^1$ is $C_2H_4$, $R^2$ is $CH_3$ and n is 15. The compound is etherified with a methyl group at its terminal. Further, "lauric acid $EO_{30}OH$", for example, in Comparative Example 7 is a comparison in which the terminal OH group is not etherified.

TABLE

|  | Compound of formula (1) | Compound of formula (2) |
|---|---|---|
| Comparative Example 1 | lauric acid $EO_{15}OMe$ | — |
| Example 1 | " | capric acid monoglyceride |
| Comparative Example 2 | lauric acid $EO_{30}OMe$ | — |
| Example 2 | " | capric acid monoglyceride |
| Example 3 | " | lauric acid monoglyceride |
| Example 4 | " | palmitic acid |

TABLE-continued

|  | Compound of formula (1) | Compound of formula (2) |
|---|---|---|
| Comparative Example 3 | myristic acid $EO_{30}OMe$ | — |
| Example 5 | " | capric acid monoglyceride |
| Example 6 | " | lauric acid monoglyceride |
| Comparative Example 4 | palmitic acid $EO_{15}OMe$ | — |
| Example 7 | " | capric acid monoglyceride |
| Example 8 | " | lauric acid monoglyceride |
| Example 9 | " | palmitic acid monoglyceride |
| Comparative Example 5 | palmitic acid $EO_{30}OMe$ | — |
| Example 10 | " | capric acid monoglyceride |
| Example 11 | " | lauric acid monoglyceride |
| Example 12 | " | palmitic acid monoglyceride |
| Comparative Example 6 | stearic acid $EO_{40}OMe$ | — |
| Example 13 | " | capric acid monoglyceride |
| Example 14 | " | lauric acid monoglyceride |
| Comparative Example 7 | lauric acid $EO_{30}OH$ | — |
| Comparative Example 8 | " | palmitic acid monoglyceride |

Each of the surfactant compositions of the above Examples and Comparative Examples was subjected to a foaming test as will be described hereinbelow.

Foaming test 100 ml of a homogeneous aqueous solution containing 3 g of the surfactant composition, 1 g of purified lanolin and 1 g of sodium chloride were mixed with care to avoid foaming. The resulting solution was transferred into a 400 ml calibrated cylinder provided with a cap as shown in FIG. 4 and allowed to stand until it was heated to about 35° C. or about 40° C. Then the cylinder was vigorously shaken 20 times within 10 seconds while holding it vertically to induce foaming. After allowing to stand for 1 minute, the foam volumes X, Y and Z were measured, wherein X means the volume of the foam above the initial liquid face, Y means the volume of the foam from the liquid face after standing to the initial liquid face, and Z means the sum of the foam volumes X and Y. In general, foams become more creamy with an increase in the ratio of the foam volume Y to the foam volume Z. Table 2 shows the results thus obtained.

TABLE 2

| | Foam volume (ml) at about 35° C. | | | | Foam volume (ml) at about 40° C. | | | |
|---|---|---|---|---|---|---|---|---|
| | X | Y | Z | (°C.) | X | Y | Z | (°C.) |
| Comparative Example 1 | 40 | 20 | 60 | (35.0) | 72 | 9 | 81 | (39.3) |
| Example 1 | 230 | 60 | 290 | (36.1) | 220 | 50 | 270 | (41.0) |
| Comparative Example 2 | 20 | 2 | 22 | (35.4) | 100 | 32 | 132 | (40.9) |
| Example 2 | 320 | 60 | 380 | (35.8) | 310 | 50 | 360 | (40.1) |
| Example 3 | 120 | 40 | 160 | (35.6) | 160 | 50 | 210 | (39.8) |
| Example 4 | 36 | 6 | 42 | (35.7) | 78 | 18 | 96 | (40.3) |
| Comparative Example 3 | 36 | 14 | 50 | (36.2) | 75 | 30 | 105 | (40.4) |
| Example 5 | 180 | 55 | 235 | (35.4) | 260 | 60 | 320 | (41.0) |
| Example 6 | 80 | 20 | 100 | (36.4) | 150 | 35 | 185 | (40.1) |
| Comparative Example 4 | 50 | 8 | 58 | (35.2) | 12 | 4 | 16 | (39.5) |
| Example 7 | 95 | 26 | 121 | (35.4) | 150 | 30 | 180 | (40.2) |
| Example 8 | 38 | 2 | 40 | (36.1) | 90 | 20 | 110 | (40.9) |
| Example 9 | 38 | 8 | 46 | (35.7) | 60 | 20 | 80 | (39.0) |
| Comparative Example 5 | 34 | 7 | 41 | (34.5) | 25 | 10 | 35 | (39.9) |
| Example 10 | 125 | 30 | 155 | (35.5) | 250 | 60 | 310 | (39.1) |
| Example 11 | 50 | 8 | 58 | (35.2) | 95 | 20 | 115 | (40.0) |
| Example 12 | 52 | 6 | 58 | (35.1) | 64 | 10 | 74 | (40.9) |
| Comparative Example 6 | 18 | 5 | 23 | (35.5) | 18 | 4 | 22 | (39.0) |
| Example 13 | 140 | 40 | 180 | (36.0) | 135 | 25 | 160 | (39.0) |
| Example 14 | 90 | 10 | 100 | (35.4) | 88 | 17 | 105 | (40.6) |
| Comparative Example 7 | 30 | 8 | 38 | (35.2) | 20 | 8 | 28 | (39.5) |
| Comparative Example 8 | 26 | 6 | 32 | (35.2) | 6 | 6 | 12 | (39.1) |

Note:
Each value given in parentheses means the accurate measurement temperature.

As the data presented in Table 2 show, the combined use of lauric acid $EO_{15}OME$ as the nonionic surfactant of formula (1) with a fatty acid monoglyceride of formula (2) generally cause an increase in the foam volume compared to the case where $EO_{15}OMe$ was used alone (measured at about 35° C.). When the temperature was elevated from about 35° C. to about 40° C., a large change in the foam volume was observed in the instance where $EO_{15}OMe$ was used alone, while the combined use caused little change in the foam volume. These facts indicate that the latter surfactant composition showed a higher foam stability against temperature change.

Regarding the fatty acid monoglycerides of formula (2), the combined use of the nonionic surfactant of formula (1) with capric monoglyceride (Example 1 and Comparative Example 1) resulted in excellent foam properties. When the EO addition mole number was increased from 15 to 30 (Examples 2 to 4 and Comparative Example 2), the combined use with capric acid monoglyceride resulted in the most excellent foaming properties, compared to the cases where lauric acid monoglyceride or palmitic acid monoglyceride was used.

When myristic acid $EO_{30}OMe$ (Examples 5 and 6 and Comparative Example 3), palmitic acid $EO_{15}OMe$ (Examples 7 to 9 and Comparative Example 4), palmitic acid $EO_{30}OMe$ (Examples 10 to 12 and Comparative Example 5) and stearic acid $EO_{40}OMe$ (Examples 13 and 14 and Comparative Example 6) were used as the nonionic surfactant of formula (1), a tendency similar to the one observed using lauric acid $EO_{30}OMe$ was observed in each case. Namely, the most excellent foaming properties were achieved using capric acid monoglyceride together with the nonionic surfactant and the combined use with lauric acid monoglyceride was preferred from the viewpoint of creamy foaming.

Further, when lauric acid $EO_{30}OH$, the terminal OH group of which is not etherified, was used as the nonionic surfactant of formula (1) (Comparative Examples 7 and 8), the foaming properties of the resulting composition were poor.

EXAMPLE 15

The components (1) to (9) listed in the following Table 3 were homogeneously mixed to provide a facial cleanser.

TABLE 3

| | Component | Content (% by weight) |
|---|---|---|
| (1) | Lauric acid polyoxyethylene methyl ether (EO addition mole number: 20, total molecular weight: 1100) | 20.0 |
| (2) | Lauric acid monoglyceride (Sunsoft 750H, a product of Taiyo Kagaku K.K.) | 8.0 |
| (3) | Monosodium citrate | 0.1 |
| (4) | Propylene glycol | 4.0 |
| (5) | Magnesium stearate | 0.1 |
| (6) | Alkox E-100 (Alkox E-100, a product of Meisei Kagaku Kogyo K.K.) | 0.1 |
| (7) | Preservative (methyl parabenzoate) | appropriate amount |
| (8) | Perfume | appropriate amount |
| (9) | Purified water | balance |
| | Total | 100.0 |

The facial cleanser thus obtained showed sufficient foaming and very little irritation to the skin and eyes.

EXAMPLE 16

The components (1) to (9) listed in the following Table 4 were homogeneously kneaded and molded to give a soap-like solid detergent.

TABLE 4

| | Component | Content (% by weight) |
|---|---|---|
| (1) | Coconut fatty acid polyoxyethylene methyl ether (EO addition mole number: 25, total molecular weight: 1350) | 55.0 |
| (2) | Lauric acid monoglyceride (Sunsoft 750H, a product of Taiyo Kagaku K.K.) | 25.0 |
| (3) | Capric acid monoglyceride (Sunsoft 760, a product of Taiyo Kagaku K.K.) | 4.0 |
| (4) | Sorbitol powder | 1.2 |
| (5) | Dipotassium glycyrrhetinate | 0.02 |
| (6) | Solid paraffin | 0.05 |
| (7) | Soluble starch | 15.0 |
| (8) | Perfume | appropriate amount |
| (9) | Purified water | balance |
| | Total | 100.0 |

The soap-like solid detergent thus obtained showed sufficient foaming and very little irritation to the skin and eyes.

The surfactant composition of the present invention shows sufficient foaming properties and scarcely irritates the skin or mucosae. Accordingly, the use of the surfactant composition of the present invention, as the main component of a soap or a shampoo, results in little irritation to the skin and mucosae, excellent foaming and a satisfactory feel to the skin.

While the invention has been described in detail and with reference to specific examples thereof, it will be apparent to one skilled in the art that various changes and modifications can be made therein without departing from the spirit and scope thereof.

What is claimed is:

1. A surfactant composition comprising a fatty acid polyoxyalkylene lower alkyl ether represented by formula (1):

$$R(OR^1)_nOR^2 \qquad (1)$$

wherein R represents an alkanoyl or alkenoyl group having from 10 to 18 carbon atoms;

$R^1$ represents an alkylene having from 2 to 4 carbon atoms;

$R^2$ represents a lower alkyl group; and n is from 5 to 100 on the weight-average; and a fatty acid monoglyceride represented by formula (2):

$$R^3OCH_2CH(OH)CH_2OH \qquad (2)$$

wherein $R^3$ represents an alkanoyl group having from 8 to 16 carbon atoms or an alkenoyl group having from 12 to 22 carbon atoms.

2. The surfactant composition of claim 1, wherein the weight ratio of the fatty acid polyoxyalkylene lower alkyl ether of formula (1) to the fatty acid monoglyceride of formula (2) ranges from 10:1 to 1:2.

3. The surfactant composition of claim 1, wherein the group $R^1$ in formula (1) is ethylene and the group $R^2$ in formula (1) is methyl.

4. The surfactant composition of claim 3, wherein the group R in formula (1) is lauroyl or myristoyl.

5. The surfactant composition of claim 1, wherein group $R^3$ in formula (2) is decanoyl or lauroyl.

6. The surfactant composition of claim 1, wherein said fatty acid polyoxyalkylene lower alkyl ether of formula (1) and said fatty acid monoglyceride of formula (2) are present in a total amount of from 0.5 to 100% by weight in terms of the final content of surfactants (1) and (2) in a final preparation.

7. A method for improving the foaming properties of a fatty acid polyoxyalkylene lower alkyl ether represented by formula (1):

$$R(OR^1)_nOR^2 \qquad (1)$$

wherein R represents an alkanoyl or alkenoyl group having from 10 to 18 carbon atoms;

$R^1$ represents an alkylene having from 2 to 4 carbon atoms;

$R^2$ represents a lower alkyl group; and n is from 5 to 100 on the average, which comprises adding a fatty acid monoglyceride represented by formula (2):

$$R^3OCH_2CH(OH)CH_2OH \qquad (2)$$

wherein $R^3$ represents an alkanoyl group having from 8 to 16 carbon atoms or an alkenoyl group having from 12 to 22 carbon atoms;

to the fatty acid polyoxyalkylene lower alkyl ether.

8. The method of claim 7, wherein the fatty acid monoglyceride is added in such a manner as to give a ratio of the fatty acid polyoxyalkylene lower alkyl ether of formula (1) to the fatty acid monoglyceride of formula (2) of from 10:1 to 1:2.

9. The method of claim 8, wherein the group $R^1$ in formula (1) is ethylene and the group $R^2$ therein is methyl.

10. The method of claim 8, wherein the group R in formula (1) is lauroyl or myristoyl.

11. The method of claim 13, wherein the group $R^3$ in formula (2) is decanoyl or lauroyl.

* * * * *